United States Patent [19]

Iwamoto

[11] Patent Number: 5,042,940
[45] Date of Patent: Aug. 27, 1991

[54] OPTICAL MEASURING APPARATUS FOR EXAMINING EYE

[75] Inventor: Masakatsu Iwamoto, Kagawa, Japan

[73] Assignee: Ryusyo Industrial Co., Ltd., Osaka, Japan

[21] Appl. No.: 416,368

[22] Filed: Oct. 3, 1989

[30] Foreign Application Priority Data

Oct. 11, 1988 [JP] Japan ............................. 63-255635
Oct. 11, 1988 [JP] Japan ............................. 63-255636

[51] Int. Cl.$^5$ ............................. A61B 3/14; A61B 3/10
[52] U.S. Cl. ..................................... 351/208; 351/211
[58] Field of Search ............... 351/208, 211, 212, 221, 351/206; 354/62

[56] References Cited

U.S. PATENT DOCUMENTS 4,678,297  7/1987  Ishikawa et al. ................. 351/208
4,712,894  12/1987  Nunokawa .
4,744,648  5/1988  Kato et al. ........................ 351/211
4,817,620  4/1989  Katsuragi et al. .

FOREIGN PATENT DOCUMENTS 63-65842  3/1988  Japan .

Primary Examiner—Rodney B. Bovernick
Attorney, Agent, or Firm—Joseph W. Price

[57] ABSTRACT

An optical measuring apparatus for examining an eye which automatically aligns the optical axes of said apparatus and the eye with each other and focusing the light emitted by said apparatus on the eye. When these operations are accomplished, the projection of a measuring light is automatically started. The apparatus includes axes-aligning-focusing optical system. The optical system has a pair of optical axes-aligning light sources. Two images of beams emitted by the respective optical axes-aligning light sources and reflected by the cornea of the eye are detected by a light receiving sensor when the beams are focused substantially on the eye. Discriminating devices discriminate whether or not the optical axes of the two cornea-reflected images detected by the light receiving sensor align with the optical axis of the eye in Y-direction of the light receiving sensor. Discriminating devices discriminate whether or not the optical axes of the two cornea-reflected images detected by the light receiving sensor align with the optical axis of the eye in X-direction of the light receiving sensor. It is not until the optical axes-aligned and in-focus states are obtained that the measuring light is projected on the eye.

4 Claims, 7 Drawing Sheets

OPTICAL MEASURING APPARATUS FOR EXAMINING EYE

BACKGROUND OF THE INVENTION

1. Field of the Invention

The present invention relates to an optical measuring apparatus for measuring an eye, and more particularly, to an optical measuring apparatus for automatically measuring various optical characteristic such as the refractive power of the eye, the curvature of the cornea or the like.

2. Description of the Related Art

An automatic refractometer (apparatus for automatically measuring the refractive power of an eye) and an automatic keratometer (apparatus for automatically measuring the curvature of a cornea) and the like are known as optical apparatuses for examining an eye. According to these apparatuses, a measuring optical system is constructed by having the eye disposed at a predetermined position of the optical axis thereof. The disposition of the eye requires the following two conditions: The optical axis of the apparatus is aligned by the optical axis of the eye, i.e., optical axes-aligned condition is obtained and the focal point of the optical system of a monitoring camera provided in the apparatus coincides with the eye disposed on the measuring optical system of the apparatus, i.e., an in-focus condition is obtained. The automatic refractometer observes, through the optical system, an optical target (measuring light) whose image is formed on the eyeground of the eye, namely, on the retina, thus automatically measuring the refractive power of the eye. In order to measure the refractive power of the eye, before the measuring lights are projected, the positions of the measuring optical system of the apparatus and the eye are adjusted to a measurable condition, namely, a condition in which optical axes of the optical system and the eye align with each other and the measuring lights projected by the light projecting optical system are focused on the eye. According to known automatic refractometers, before the examination of the eye is started, the apparatus is moved lengthwise and widthwise so that the position of an axes-aligning mark (reticle pattern) and the position of the image of a light reflected by the cornea displayed on the monitor screen align with each other. Thus, an optical axes alignment is accomplished. In addition, the distance between the apparatus and the eye is adjusted. Thus, the focal point of the optical system of the monitoring camera of the apparatus coincides with the position of the eye disposed on the measuring optical system thereof. As described above, in order to measure the refractive power of the eye, it is necessary for an operator to confirm that optical axes-aligned and in-focus condition have been obtained on the monitor screen and then, to turn on a measuring start switch.

However, according to the above-described method for examining the eye, it is difficult for a patient to keep the same posture when optical axes-aligned and in-focus conditions have been obtained. In practice, it is very difficult for the operator to turn on the switch immediately after the optical axes-aligned and in-focus conditions are obtained. That is, the operator must be skilled in the timing of turning on the measuring start switch.

SUMMARY OF THE INVENTION

It is an object of the present invention to provide an optical measuring apparatus for examining an eye provided with a mechanism capable of reliably obtaining axes-aligned and in-focus conditions in an appropriate timing.

In accomplishing this and other objects, according to one preferred embodiment of the present invention, there is provided an improved apparatus for measuring an eye, for example the refractive power of an eye, which comprises having a measuring light projecting system for projecting a measuring light on an eye; a measuring light receiving system including a light receiving sensor which receives a light reflected by the eye; optical axes-aligning-focusing means including an axes-aligning-focusing system for aligning the optical axes of the apparatus and the eye with each other and focusing the light emitted by the apparatus on the eye; measuring means for projecting a measuring light on the eye and measuring the eye based on a light reflected by the eye and received by the measuring optical system. The optical measuring apparatus has the following feature. The light receiving sensor is so disposed that the optical axis of the measuring light receiving system passes through the intersection section of an X-axis and Y-axis provided on the light receiving sensor. The axes-aligning-focusing optical system includes a pair of optical axes-aligning light source means for projecting beams on the eye. The pair of optical axes-aligning light source means for projecting fine beams on the cornea of the eye is disposed so that the light source means are symmetrical with respect to the optical axis B of the light receiving optical system in an X-direction and that the beam reflected by the cornea of the eye is received by the light receiving sensor only when an axes-aligned and in-focus state is substantially obtained. The optical axes-aligning-focusing means includes; first comparing means for comparing a level of cornea-reflected image received by the light receiving sensor with a reference value; discriminating means for discriminating whether or not two cornea-reflected images are received by the light receiving sensor of the X-axis thereof when the level of two cornea-reflected images exceeds the reference value by the first comparing means; calculating means for calculating the distance between the two cornea-reflected images received by the light receiving sensor and the Y-axis of the light receiving sensor; second comparing means for comparing two distances calculated by the calculating means with each other and outputting a signal indicating the start of the projection of the measuring light if the difference between the two calculated distances is less than the tolerance.

In the above-described construction, if the distance between the measuring apparatus and the eye is inappropriate, that is, if the beams emitted by the optical axes-aligning-focusing system is not focused on the eye, the optical axes aligning beams reflected by the cornea is not received by the light receiving sensor. Even if the beams are received by the light receiving sensor, the level of the signals indicating the cornea-reflected images is lower than the reference value. This condition is detected by the first comparing means. Thus, an in-focus state can be obtained. Further, when the axes-aligning error is relatively large, the cornea-reflected images are not received by the light receiving sensor. This state is also discriminated by the first comparing means. In the case where the axes-aligning error is extremely small, the mis-alignments in X-direction and Y-directions in the light receiving sensor are considered. The mis-alignment in Y-direction is detected by the discriminating means and the mis-alignment in Y-direction is detected by the calculating means and the second comparing means. Thus, an optical axes-alignment is accurately accomplished. When in-focus state and optical axes-aligned states are obtained, the second comparing means outputs to the apparatus a signal indicating that the projection of a measuring light should be started.

Therefore, according to the above-described construction, when in-focus state and optical axes-aligned states are obtained, the examination of the eye is immediately started. Thus, an appropriate measuring timing can be obtained.

According to another preferred embodiment in accordance with the present invention, the axes-aligning-focusing system has a pair of optical axes-aligning light source means for projecting a pair of beams close to each other and arranged in X-direction on the eye. The pair of optical axes-aligning light source means is disposed to be symmetrical with respect to the optical axis in X-direction. The optical axes-aligning-focusing means includes a first discriminating means for discriminating whether or not cornea-reflected images are formed on the light receiving sensor on the X-axis thereof; a second discriminating means for discriminating whether or not cornea-reflected images, formed on the light receiving sensor on the X-axis thereof and detected by the first discriminating means, do not overlap with each other and are separated from each other; and a calculating means for calculating the distances between the Y-axis of the light receiving sensor and each of two images disposed on both outer sides among four images received by the light receiving sensor on the X-axis thereof; and comparing means for comparing two distances calculated by the calculating means with each other and outputting a signal indicating the start of the projection of the measuring light if the difference between the two calculated distances is within the tolerance.

In the above-described construction, an optical axes alignment in a Y-direction of the light receiving sensor is carried out by the first discriminating means and a focusing adjustment is performed by the second discriminating means. That is, the first discriminating means detects whether or not a cornea-reflected image is formed on the X-direction of the light receiving sensor. Thus, an optical axes alignment in a Y-direction in the light receiving sensor is effected. The second discriminating means detects whether or not four images reflected by the cornea do not overlap with each other or are separated on the light receiving sensor, thus discriminating whether or not the lights emitted by the optical axes-aligning-focusing means is focused on the eye. The calculating means and the comparing means detect whether or not the four images, namely, a pair of cornea-reflected images received by the X-axis on the left and right sides thereof are symmetrical with respect to the Y-axis thereof. That is, the calculating means and the comparing means detects an optical axes-aligned state. When the optical axes-aligned state is obtained, the comparing circuit outputs to the apparatus a signal indicating that the projection of a measuring light be started.

Similarly to the above-described construction, when the optical axes are aligned and in-focus conditions are obtained, the examination of the eye is started. Thus, an appropriate measurement timing can be always obtained.

BRIEF DESCRIPTION OF THE DRAWINGS

These and other objects and features of the present invention will become apparent from the following description taken in conjunction with the preferred embodiments thereof with reference to the accompanying drawings, in which.

DETAILED DESCRIPTION OF THE INVENTION

Figure 1:
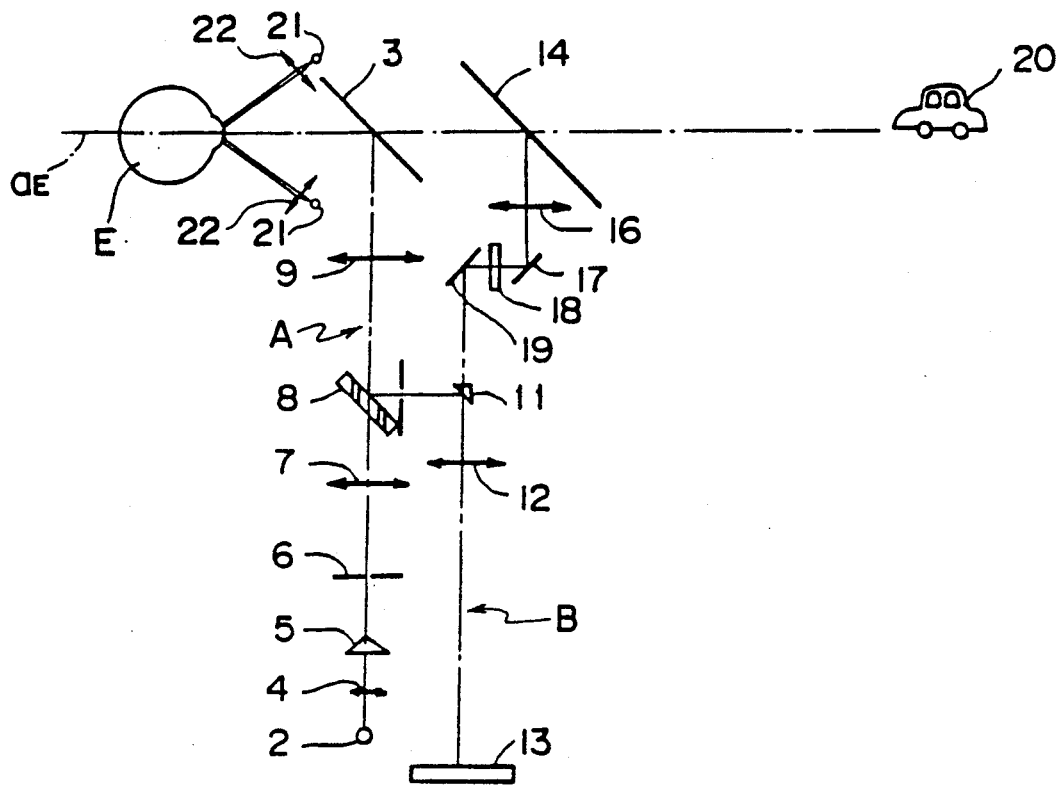
FIG. 1 is an illustration of the optical system of an automatic refractometer, used as an optical measuring apparatus for examining an eye, in accordance with one embodiment of the present invention.

Before the description of the present invention proceeds, it is to be noted that like parts are designated by like reference numerals throughout the accompanying drawings.

Figure 2:
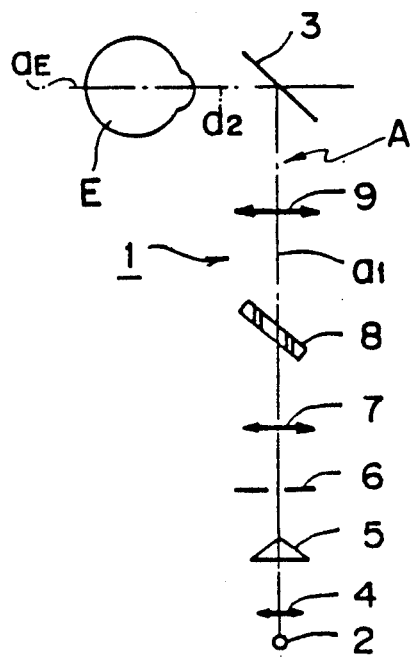
FIG. 2 shows a measuring light projecting optical system included in the optical system shown in FIG. 1.
Figure 3:
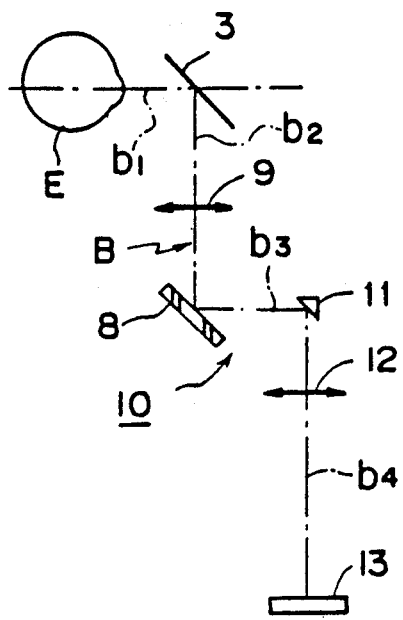
FIG. 3 shows a light receiving optical system included in the optical system shown in FIG. 1.
Figure 4:
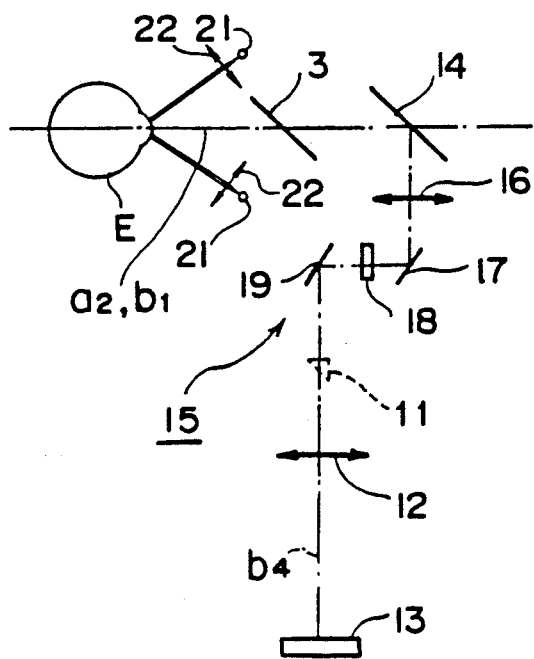
FIG. 4 shows an optical axes-aligning-focusing optical system included in the optical system shown in FIG. 1.
Figure 5:
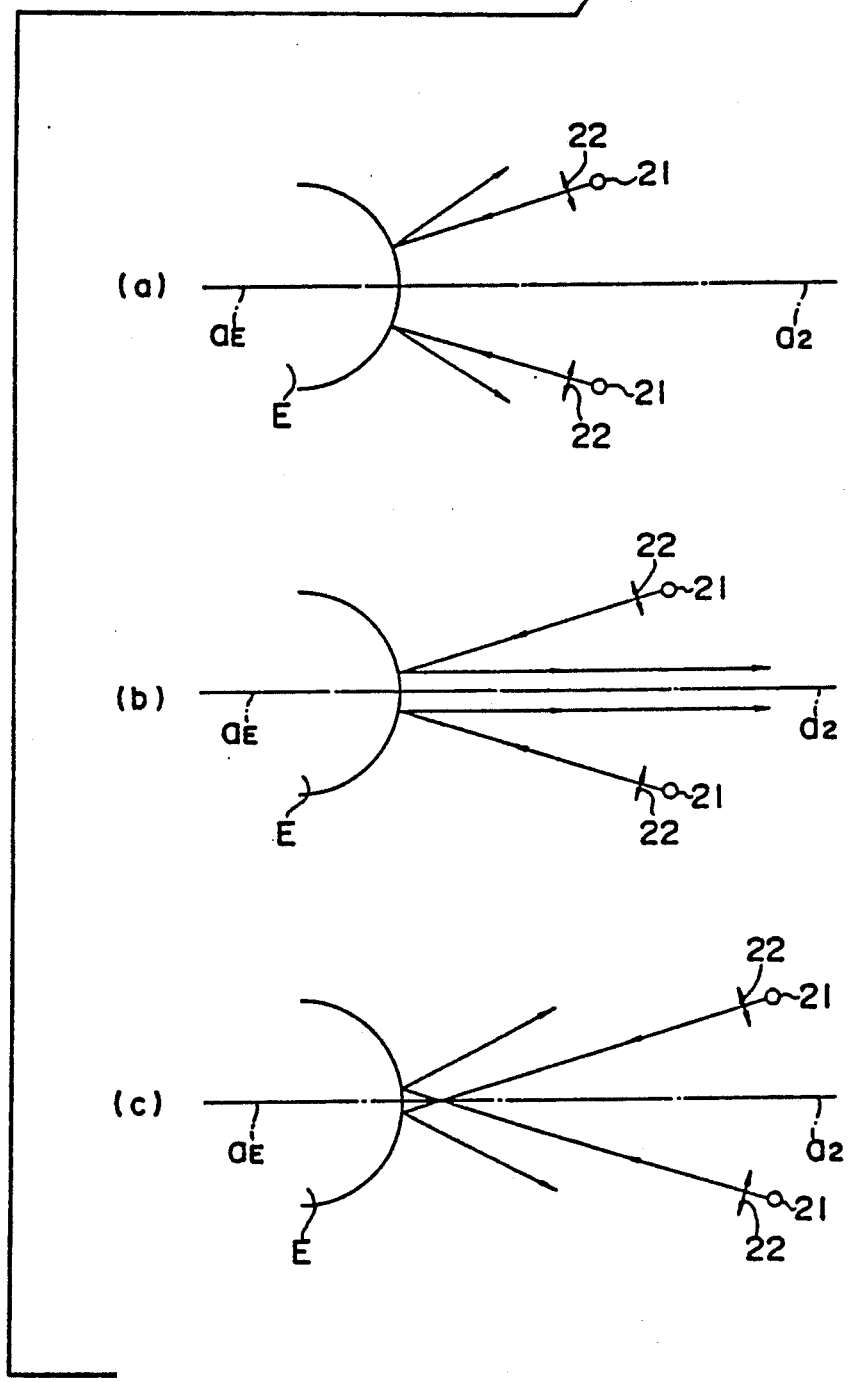
FIG. 5 (a), (b), and (c) show the relationship between the positions of the eye and the optical axes-aligning light source of the automatic refractometer shown in FIG. 1.

Referring now to FIGS. 1 through 9, a first embodiment of the present invention is described hereinafter. FIG. 1 is an illustration showing the entire optical system of an automatic refractometer of an optical measuring apparatus for examining an eye (hereinafter referred to as apparatus) in accordance with a first embodiment of the present invention. FIG. 2 shows a measuring light projecting optical system shown in FIG. 1. FIG. 3 shows a light receiving optical system shown in FIG. 1. FIG. 4 shows an optical axes-aligning-focusing optical system shown in FIG. 1.

The optical axis (A) of the measuring light projecting optical system extends from a light source 2 to a first half mirror 3 and is reflected by a first half mirror 3 at an angle of 90°, then travels to an eye to be examined (hereinafter referred to as eye E). An infrared ray emitting diode is used as the light source 2. Various optical elements are disposed along an optical axis $a_1$ extending rectilinearly from the light source 2 to the first half mirror 3. A measuring light emitted by the light source 2 is reflected by the first half mirror 3, thus traveling from the apparatus to the eye E along an optical axis $a_2$. That is, the measuring light can be projected into the eye E by disposing the optical axis $a_E$ of the eye E on the optical axis $a_2$. The following optical elements are disposed along the optical axis $a_1$ between the light source 2 and the first half mirror 3 in the following order: a collimator lens 4, a quadrangular pyramid prism 5, a diaphragm 6, a light projecting lens 7, a four-opening mirror 8, and an eyepiece 9. In order to form four spot patterns of the measuring light, the quadrangular pyramid prism 5 disperses an infrared ray which has been emitted by the light source 2 and passed through the collimator lens 4 into four beams concentrically spaced from each other at an angular interval of 90° in the periphery of the optical axis $a_1$. The diaphragm 6 is disposed at the focal point of the light projecting relay lens 7. Therefore, the four beams which have been dispersed by the quadrangular pyramid prism 5 pass through the diaphragm 6, and thereafter, are incident on the light projecting relay lens 7. Then, the four beams become parallel with the optical axis $a_1$, thus forming four spot patterns. In the light receiving optical system 10 which is described later, the four-opening mirror 8 reflects the measuring light reflected by the retina of the eye E at an angle of 90°, the upper face of which forms 45° with the optical axis $a_1$. In the light projecting optical system 1, four small openings are formed on the four-opening mirror 8 at the portions corresponding to the light paths of the four spot patterns so that the four-opening mirror 8 does not intercept the optical path of the four spot patterns. Thus, the measuring lights which have passed through the openings of the four opening mirror 8 are incident on the eyepiece 9 as four spot patterns. Then, the measuring lights are reflected at an angle of 90°, thus entering into the eye E. The optical axes $b_1$ and $b_2$ disposed from the eye E to the four-opening mirror 8 and forming part of optical axis (B) of the light receiving system 10 coincide with the optical axes $a_2$ and $a_1$ of the optical axis (A) of the light projecting system 1, respectively.

In the light, receiving optical system, the measuring lights reflected by the retina travel backward to the of the four-opening mirror 8 along the optical axes $b_1$ and $b_2$, thus being reflected by the four-opening mirror 8 at an angle of 90°. A micromirror 11 having a face parallel with the faces of the four-opening mirror 8 is disposed on the optical axis $b_3$ of the reflected measuring lights. The micromirror 11 reflects the reflected measuring lights downward at right angles with the optical axis $b_3$. There is provided below the micromirror 11 an image forming lens 12 and a light receiving sensor 13 composed of a CCD (charge coupled device) serving as an image sensor matrix along an optical axis $b_4$. The optical axis $b_4$ pass through the center of the light receiving sensor 13. Therefore, supposing that the cross section of the space through which a light passes is a field, the center of the field is disposed on the optical axis (B) of the light receiving optical system 10. In other words, the optical axis (B) or $b_4$ passes through the intersection, of the X- axis and Y-axis on the light receiving sensor 13.

In the optical axes-aligning-focusing optical system 15, a pair of an optical axes-aligning light sources 21, 21 comprising an infrared ray emitting diode is horizontal and symmetrical with respect to the optical axis $a_2$. The direction of a straight line formed by connecting both the optical axes-aligning light sources 21 and 21 coincides with the direction in which the field is scanned on the light receiving sensor 13. Normally, when the image in the field is monitored, a scanning line moves downward sequentially while the field is scanned widthwise in the monitor screen. In this embodiment, the image in the field is scanned widthwise, i.e., the scanning direction is from left to right as viewed from an operator. The diameter of lights emitted by the optical axes-aligning light source 21 are greatly reduced into light beams by the collimator lens 22 disposed forward of the optical axes-aligning light source 21. When the eye E is appropriately disposed for an examination, the beams reflected by the cornea travels back in parallel with the optical axis $a_2$. Thus, the beams are detected by the light receiving sensor 13.

FIGS. 5(a), 5(b), and 5(c) show directions, of lights reflected by the cornea, which differ from each other depending on the distance between the eye E and the optical axes-aligning light source 21. FIG. 5(a) shows the case in which the distance therebetween is too short. FIG. 5(a) shows the case in which the distance therebetween is appropriate enough to be examined. FIG. 5(c) shows the case in which the distance therebetween is too long. As understood from these figures, each of the diameters of the beams emitted by the respective optical axes-aligning light sources is very small and each of the areas of spots of the beams is very small on the cornea. Therefore, each of the diameters of beams reflected by the cornea is small and as such, does not diffuse. Thus, If the optical axes-aligning light source 21 is too far from or near to the eye E, the distance between the optical axis $a_2$ and the beams reflected by the cornea becomes great as the beams travel forward from the eye E. On the other hand, when the distance between the eye E and the optical axes-aligning light source 21 is appropriate, the beams reflected by the cornea travel substantially parallel with the optical axis $a_2$, thus reaching the light receiving sensor 13. In this embodiment, the focal point of the optical system of a monitoring camera coincides with the cornea when the distance between the optical axes-aligning light source 21 and the eye E is as shown in FIG. 5(b).

Meanwhile, when the error of focusing condition is extremely small, the reflected lights from the cornea can be received by the light receiving sensor 13.

The optical elements constituting the optical path of beams emitted by the optical axes-aligning light source 21 and reflected by the cornea (hereinafter referred to as optical axes-aligning beam) are described hereinafter. An optical axes aligning beam partially pass through the first half mirror 3 is reflected downward at an angle of 90° by a second half mirror 14, then passes through a monitor relay lens 16. A first 45° mirror 17 is disposed below the monitor relay lens 16. The beam which has passed through the mirror 17 is incident on a reticle plate 18 made of a transparent glass on which a reticle pattern is drawn. The reticle plate 18 is conjugate with the eye E with respect to the monitor relay lens 16. The beam which has passed through the reticle plate 18 is incident on a second 45° mirror 19 which reflects the beam downward at an angle of 90°. The light receiving optical system 10 and the optical axes-aligning-focusing optical system 15 have in common the optical axis $b_4$ disposed below the second 45° mirror 19 and including the image forming lens 12 and the light receiving sensor 13. Accordingly, the optical axes aligning-focusing-optical system 15 has a construction in which the monitoring reticle optical system is incorporated in the optical system of the monitoring camera. The micromirror 11 of the optical axes aligning-focusing-optical system 15 is so small that the optical axes aligning beams travel in the periphery thereof. Thus, the micromirror 11 causes no problem in measuring the refractive power of the eye E. As shown in FIG. 1, a target 20 is disposed on the extension of the optical axis $a_2$ of the light projecting optical system 1 so that a patient watches a far point in having the refractive power of the patient's eye E examined.

Figure 6:
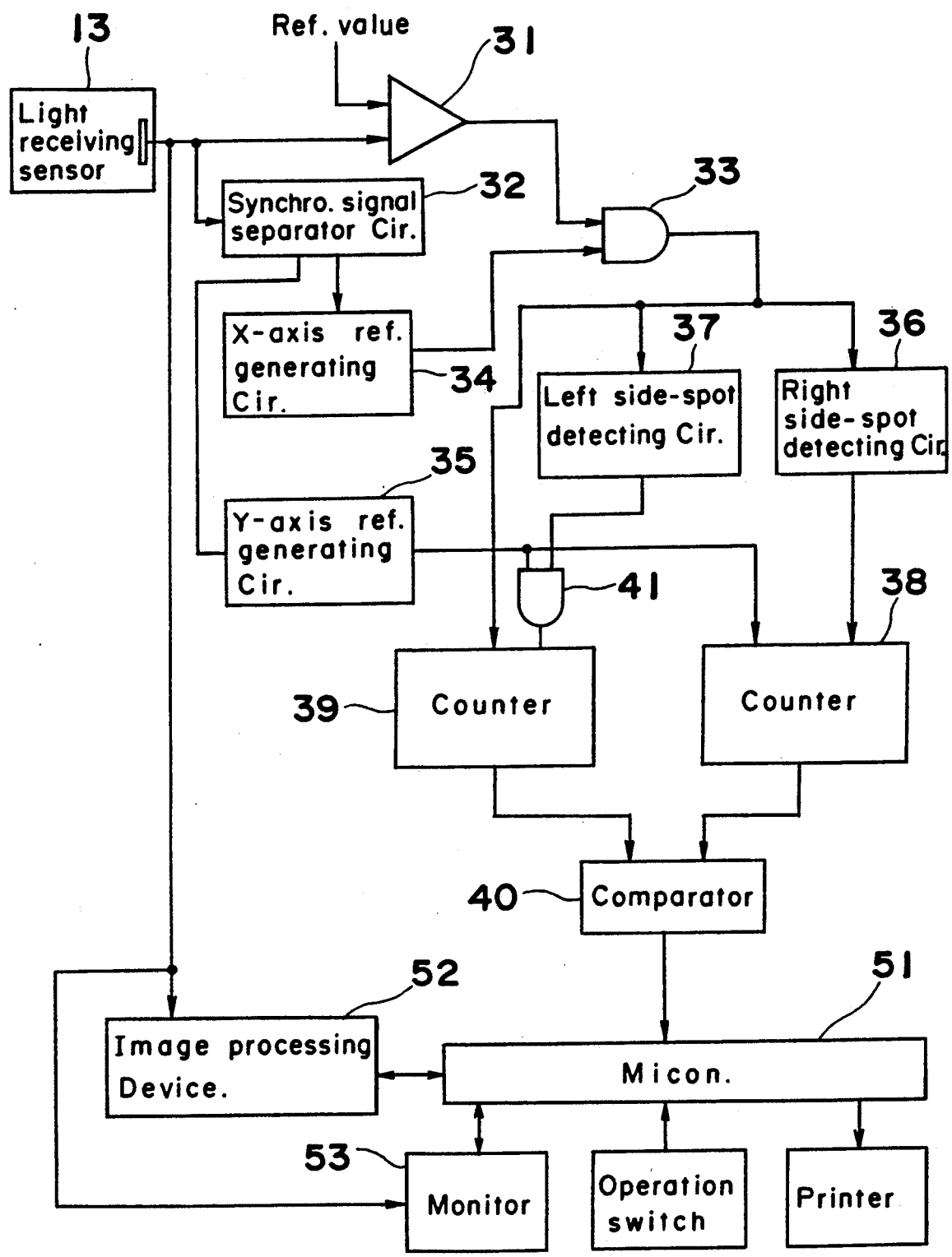
FIG. 6 is a block diagram of the automatic refractometer shown in FIG. 1.

FIG. 6 is a block diagram of the automatic refractometer. The measuring beams (emitted by the light source 2) reflected by the retina and beams (emitted by the optical axes-aligning light source 21) reflected by the cornea are received by the light receiving sensor 13 to be scanned, thus sequentially converting the beams into image signals (electric signals). Together with synchronizing signals of the scanning, the image signals are inputted to a comparator 31, a synchronizing signal separator circuit 32, an image processing device 52, and a monitor 53.

The image signals inputted to the comparator 31 are outputted to an AND circuit 33 in two different levels. That is, one level is higher and the other level is lower than a reference value set in the comparator 31. The reference value substantially corresponds to the luminance of the optical axes-aligning light source 21. That is, the level of the signal corresponding to the image of the measuring beam reflected by the retina is lower than the reference value and the signal corresponding to the image of the optical axes-aligning beam reflected by the cornea is lower than the reference value. The synchronizing signal inputted to the synchronizing signal separator circuit 32 is separated into a horizontal synchronizing signal and a vertical synchronizing signal. The horizontal synchronizing signal is inputted to an X-axis reference generating circuit 34 and a Y-axis reference generating circuit 35. The vertical synchronizing signal is inputted to only the X-axis reference generating circuit 34. In the X-axis reference generating circuit 34, based on the horizontal synchronizing signal and the vertical synchronizing signal, timing signals representing the X-axis which passes through the center of the optical axis are generated and inputted to the AND circuit 33. The Y-axis reference generating circuit 35 includes a clock pulse generating circuit and a pulse counter. The Y-axis reference generating circuit 35 outputs a timing signal to the AND circuit 41 and a counter 38 for detecting the distance of the right side-spot with respect to Y-axis when the number of pulses counted from the point the horizontal synchronizing signal coincides with Y-axis which passes through the center of the optical axis. The AND circuit 33 outputs signals to a right side-spot detecting circuit 36, a left side-spot detecting circuit 37, and a counter 39 for detecting the distance of the left side-spot with respect to Y-axis only when the signal outputted from the comparator 31 is disposed on X-axis, namely, the reference axis. The signal corresponding to the beam emitted by the optical axes-aligning light source 21 disposed on the right side is outputted from the right side-spot detecting circuit 36. The signal corresponding to the beam emitted by the optical axes-aligning light source 21 disposed on the left side is outputted from the left side-spot detecting circuit 37. That is, the left side-spot detecting circuit 37 comprising a one-pulse counter outputs a signal to the AND circuit 41 when one pulse signal is inputted thereto from the AND circuit 33. The right side-spot detecting circuit 36 comprising a two-pulse counter outputs a signal to the counter 38 when two pulse signals are inputted thereto from the AND circuit 33.

The counters 38 and 39 serve as means for measuring the distance between Y-axis and the right side-spot image of the beam reflected by the cornea and the distance between Y-axis and the left side-spot image of the beam reflected by the cornea. The counter 39 starts a counting in response to a signal outputted from the AND circuit 33 and terminates the counting in response to a signal outputted from the AND circuit 41. In response to signals outputted from the left side-spot detecting circuit 37 and the Y-axis reference generating circuit 35, the AND circuit 41 outputs to the counter 39 a stop signal indicating that the counting be stopped. Thus, the counter 39 terminates the counting. The counter 39 outputs to a comparator 40 a counted value corresponding to the distance between Y-axis and the left side-spot image reflected by the cornea. The counter 38 starts a counting in response to a signal outputted from the Y-axis reference generating circuit 35 and terminates the counting in response to a signal outputted from the detecting circuit 36. The counter 39 outputs to the comparator 40 a counted value corresponding to the distance between Y-axis and the right side-spot image reflected by the cornea. The comparator 40 decides whether or not the absolute values counted by the counters 38 and 39 are close to each other and within the tolerance, namely, whether or not the positions of the left side-spot image and right side-spot image of the beams reflected by the cornea are symmetrical with respect to Y-axis. If the counted values are within the tolerance, a signal indicating that a measuring can be started is outputted to a microcomputer 51, so that the microcomputer 51 outputs to the light projecting optical system 1 a signal which indicates that a measuring light should be projected.

Figure 7:
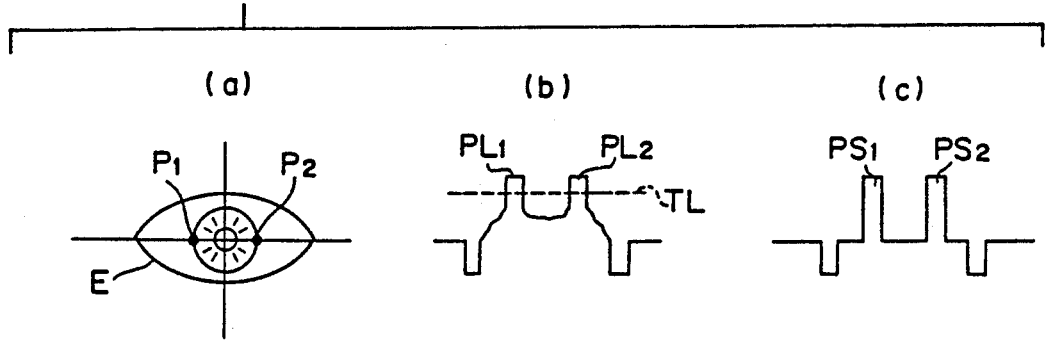
FIG. 7 shows a condition in which optical axes-aligned and in-focus states are obtained in which (a) shows an image displayed on a monitor screen; (b) shows an image signal on X-axis; and (c) shows a binary image signal on X-axis.
Figure 8:
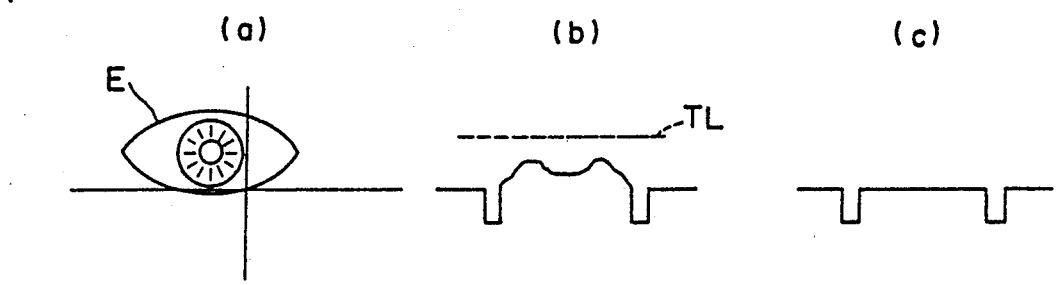
FIG. 8 shows a condition in which an in-focus state is obtained, but an optical axes-aligned state is not obtained in which (a) designates an image displayed on a monitor screen; (b) shows an image signal on an X-axis; and (c) denotes a binary image signal on the X-axis.
Figure 9:
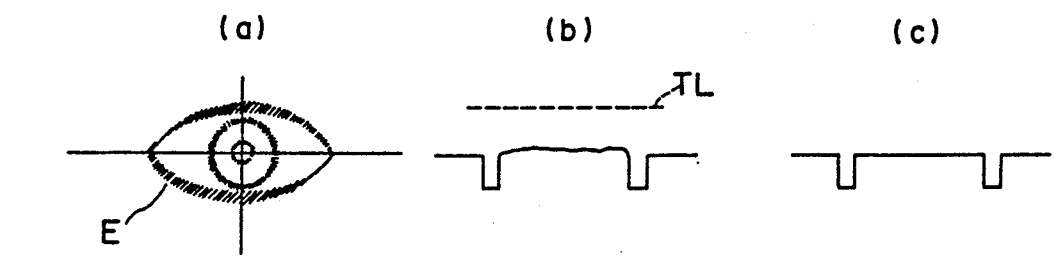
FIG. 9 shows a condition in which an optical axes-aligned state is obtained, but an in-focus state is not obtained, in which (a) designates an image displayed on a monitor screen; (b) shows an image signal an image signal on X-axis; and (c) denotes a binary image signal on the X-axis.

FIGS. 7, 8, and 9 show the following three conditions when an optical axes-alignment and a focusing are carried out. FIGS. 7(a), 8(a), and 9(a) show images of spots and the eye E displayed on the monitor 53. FIGS. 7(b), 8(b), and 9(b) show image signals detected by the light receiving sensor 13 on the X-axis thereof. FIGS. 7(c), 8(c), and 9(c) show the binary signals of the image signals. FIG. 7 shows the condition in which the optical axes of the eye E and the axes-aligning-focusing optical system 15 are aligned with each other and the beams emitted by the axes-aligning-focusing optical system are focused on the eye E. FIG. 8 shows the condition in which the beams emitted by the axes-aligning-focusing optical system are focused on the eye E, but optical axes of the eye E and the axes-aligning-focusing optical system 15 are not aligned with each other. FIG. 9 shows the condition in which the optical axes of the eye E and the axes-aligning-focusing optical system 15 are aligned with each other, but the beams emitted by the axes-aligning-focusing optical system are not focused on the eye E.

As shown in FIG. 7, when the optical axes of the eye E and the axes-aligning-focusing optical system 15 are aligned with each other and the beams emitted by the axes-aligning-focusing optical system are focused on the eye E, the images of the eye E and the spot images of the optical axes-aligning beams are clearly displayed on the center of the monitor. In particular, the spot images $P_1$ and $P_2$ formed by the optical axes-aligning beams are clearly displayed on the monitor screen. That is, as shown in FIG. 7(b), the signal outputted from the light receiving sensor 13 and corresponding to the spot images $P_1$ and $P_2$ has clear peaks $PL_1$ and $PL_2$ at the portions corresponding to the spot images $P_1$ and $P_2$. As described previously, since the reference value TL is set in the comparator 31 so as to convert the signal outputted from the light receiving sensor 13 into a high level signal and a low level signal, two pulse signals $PS_1$ nd $PS_2$ outputted from the AND circuit 33 and corresponding to the spot images $P_1$ and $P_2$ can be obtained on X-axis as shown in FIG. 7(c).

It is to be noted that, even if there is a axes-aligning error and the error is extremely small, the axes-aligning beams reflected by the cornea can be received by the light receiving sensor 13 and pulse signals $PS_{1,2}$ may be outputted from the comparator 31. In this case, however, if it is an error with respect to the Y-axis direction, it means that the spot images do not disposed on the X-axis so that no high level signal is outputted. Therefore, it is understood that the optical axes of the eye E and the axes-aligning-focusing system are not precisely aligned with each other. On the other hand, when it is an error with respect to the X-axis direction, the distances of the left side-spot and right side-spot with respect to the Y-axis are compared with each other by the comparator 40.

When the beams emitted by the axes-aligning-focusing optical system are focused on the eye E, but optical axes of the eye E and the axes-aligning-focusing optical system 15 are not aligned with each other, with exception of the case where the axes-aligning error is extremely small, the images of the eye E are clearly displayed on the monitor, while the spots of the optical axes-aligning beams are not displayed on the monitor. Therefore, the signal, corresponding to the spot images, detected by the light receiving sensor 13 on X-axis thereof is almost flat or does not have a peak having a significant peak as exceeding the reference value TL set in the comparator 31 as shown in FIG. 8(b) and the high level and low level signals produced in the comparator 31 have no pulse signals as shown in FIG. 8(c).

When the optical axes of the eye E and the optical axes-aligning-focusing system 15 are aligned with each other, but the beams emitted by the axes-aligning-focusing optical system are not focused on the eye E, the image of the eye E is displayed in the center of the monitor screen, but blurred and the spot images are not displayed on the monitor screen. This is because the optical axes-aligning beam reflected by the cornea does not reach the light receiving sensor 13 as described previously referring to FIG. 5. Accordingly, the signal detected by the light receiving sensor 13 on X-axis thereof is low in its level and has hardly any peaks as shown in FIG. 9(b). The high level and low level signals produced in the comparator 31 have no pulse signals as shown in FIG. 9(c).

It is to be noted that, when the focusing error is extremely small so that the axes-aligning beams reflected by the cornea of the eye E can be received by the light receiving sensor 13, the corresponding image signals are outputted from the sensor 13 to the comparator 31. However, the level of the signals are lower than the reference value TL so that no high level signal is outputted from the comparator 31.

According to the automatic refractometer provided with the mechanism, for aligning the optical axes of the eye E and the optical axes-aligning-focusing system with each other, which is constructed and operates as above, watching the image displayed on the monitor screen, an operator adjusts the distance between the eye E and the apparatus by moving the main body of the apparatus lengthwise and widthwise so as to alter the condition shown in FIG. 8 or FIG. 9 to the condition shown in FIG. 7. When the state shown in FIG. 7 is obtained, i.e., when optical axes-aligned and in-focus states are detected, the measuring of the refractive power of the eye E is automatically started. Thus, the automatic refractometer is capable of measuring the refractive power of the eye E in an appropriate measuring timing period.

A second embodiment of the present invention is described with reference to FIGS. 10 through 14.

Figure 10:
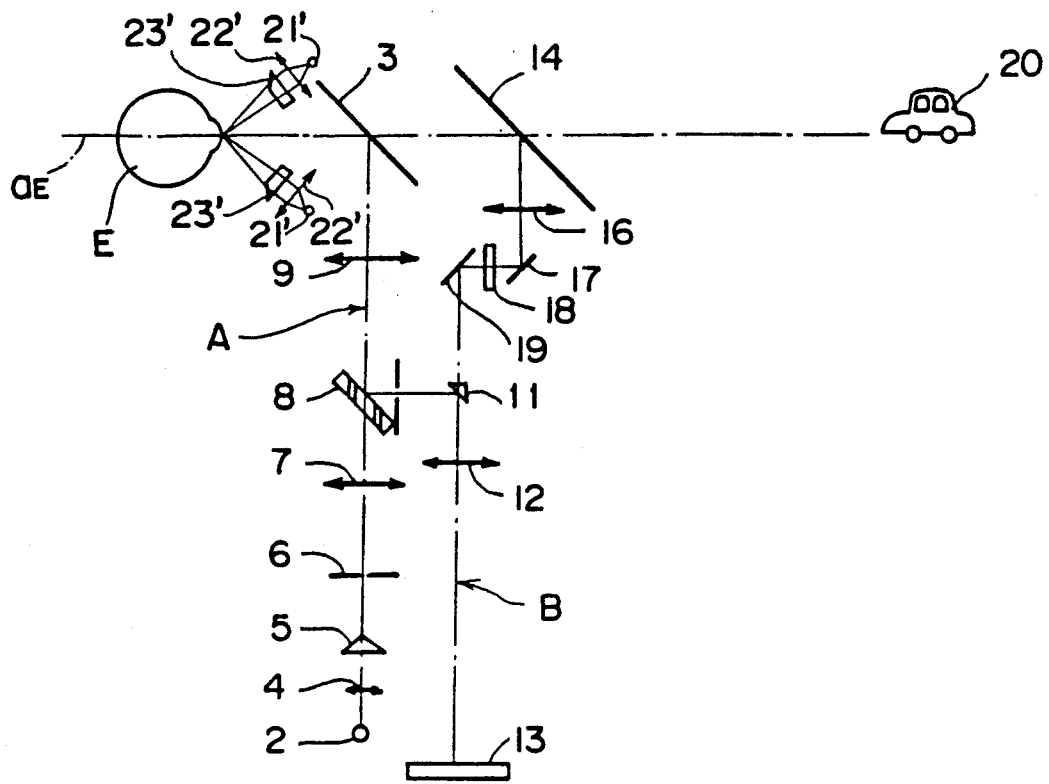
FIG. 10 shows, similarly to FIG. 1, the optical system of an automatic refractometer, according to a second embodiment of the present invention.
Figure 11:
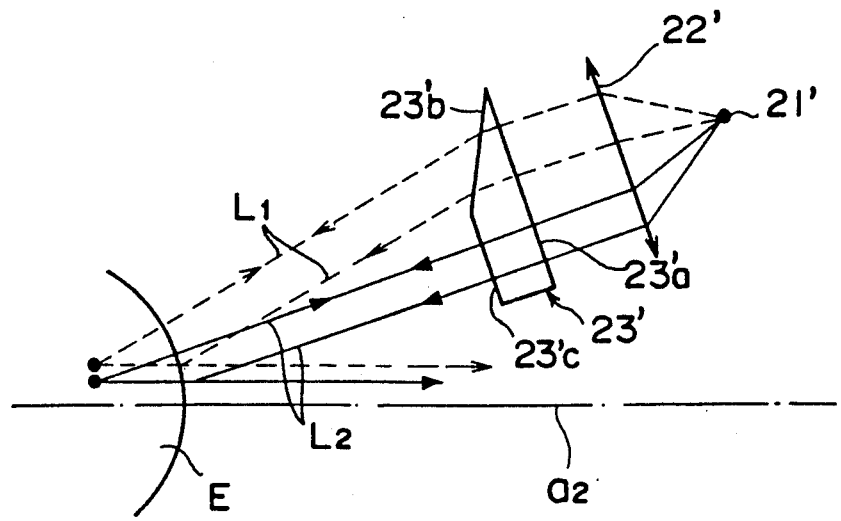
FIG. 11 is an illustration showing the relationship between an optical axes-aligning light source and an eye in an automatic refractometer shown in FIG. 10.

Similarly to the first embodiment, FIG. 10 shows the entire optical system of an automatic refractometer. Since the fundamental construction of this optical system is identical to that of the first embodiment, like parts are designated by like reference numerals and the detailed descriptions thereof are omitted. A light source means for aligning optical axis of the eye E and that of the optical axes-aligning system in accordance with the second embodiment differs from that of the first embodiment. The light source means is described hereinbelow.

The light source means comprises an optical axes-align light source 21', a collimator lens 22', and a trapezoidal prism 23'. A pair of light source means are disposed to be symmetrical with respect to an optical axis $a_2$ similarly to the first embodiment. The feature of the optical axes-aligning light sources is that a pair of beams close to each other is formed so that beams are projected on the cornea of the eye E. That is, light emitted by each of the optical axes-aligning light sources 21' comprising infrared emitting diodes is made to be light beams parallel to each other by the collimator lens 22', and then, are incident on the plane 23, of a trapezoidal prism 23', thereafter, travel forward through different planes 23'b and 23'c in the form of two beams $L_1$ and $L_2$. The trapezoidal prism 23' forms the beams $L_1$ and $L_{2_2}$ so that spot images of the beams $L_1$ and $L_2$ reflected by the cornea are clearly formed on the light receiving sensor 13 in such a condition that the spot images do not overlap with each other thereon when the focal point of the optical axes-aligning-focusing system coincides with the eye E, i.e., when beams emitted by the optical axes-aligning/focusing system is focused on the eye E.

Instead of the trapezoidal prism 23' employed in the second embodiment, other means may be used to form two light beams close to each other. For example, two collimator lens 22' may be arranged in the same plane.

As described above, in the second embodiment, four spot images, namely, two pairs of spot images close to each other are formed on the light receiving sensor 13 by two optical axes-aligning light source means. Therefore, the left side-spot detecting circuit 37 provided in the block diagram of the automatic refractometer, as shown in FIG. 6, comprises a two-pulse counter and the right side-spot detecting circuit 36 provided therein comprises a four-pulse counter. The block diagram of the second embodiment is identical to that of the first embodiment (FIG. 6) except the right side-spot detecting circuit 36 and the left side-spot detecting circuit 37.

The optical axes-aligning and focusing operations of the second embodiment are described with reference to FIGS. 12 through 14.

Figure 12:
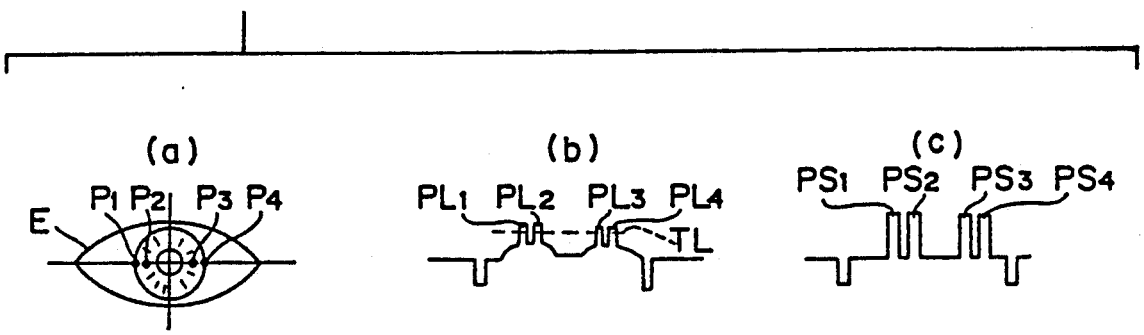
FIGS. 12 (a), 12 (b), 12(c), 13(a), 13(b), 13(c), 14(a), 14(b), and 14(c) are illustrations showing the second embodiment and being similar, respectively, to FIGS. 7(a), 7(b), 7(c), 8(a), 8(b), 8(c), 9(a), 9(b), and 9(c).
Figure 13:
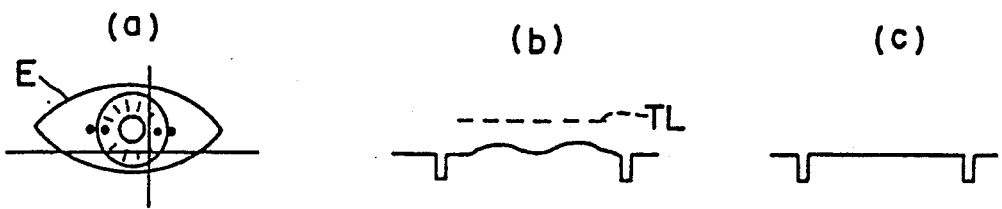
Figure 14:
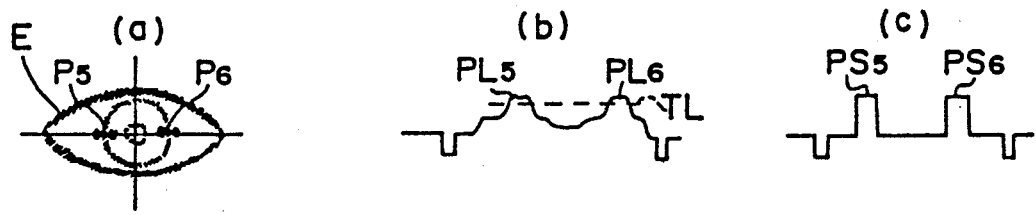

FIGS. 12 through 14 correspond to FIGS. 7 through 9 of the first embodiment. FIGS. 12, 13, and 14 show the following three conditions when an optical axes-alignment and a focusing are carried out. Figs. 12(a), (13a), and 14(a) show images of spots and the eye E displayed on the monitor 53. FIGS. 12(b), 13(b), and 14(b) show image signals detected by the light receiving sensor 13 on the X-axis thereof FIGS. 12(c), 13(c), and 14(c) show the binary signals of the image signals. FIG. 12 shows the condition in which the optical axes of the eye E and the axes-aligning-focusing optical system 15 are aligned with each other and the beams emitted by the axes-aligning-focusing optical system are focused on the eye E. FIG. 13 shows the condition in which the beams emitted by the axes-aligning-focusing optical system are focused on the eye E, but optical axes of the eye E and the axes-aligning-focusing optical system 15 are not aligned with each other. FIG. 14 shows the condition in which the optical axes of the eye E and the axes-aligning-focusing optical system 15 are aligned with each other, but the beams emitted by the axes-aligning-focusing optical system are not focused on the eye E.

As shown in FIG. 12, when the optical axes of the eye E and the axes-aligning-focusing optical system 15 are aligned with each other and the beams emitted by the axes-aligning-focusing optical system are focused on the eye E, the images of the eye E and the spot images of the optical axes-aligning beams are clearly displayed on the center of the monitor. In particular, the spot images $P_1$, $P_2$ and $P_3$, $P_4$ formed by the optical axes-aligning beams are clearly displayed on the left side and right side of the monitor screen, respectively. That is, as shown in FIG. 12(b), each of the signals outputted from the light receiving sensor 13 and corresponding to the spot images $P_1$ through $P_4$ has clear peaks $PL_1$ through $PL_4$ at the portions corresponding to the spot images $P_1$ through $P_4$. As described previously, since the reference value TL is set in the comparator 31 so as to convert the signal outputted from the light receiving sensor 13 into a high level signal and a low level signal, four pulse signals $PS_1$ through $PS_4$ outputted from the AND circuit 33 and corresponding to the spot images $P_1$ and $P_4$ can be obtained on X-axis as shown in FIG. 12(c).

When the beams emitted by the axes-aligning-focusing optical system are focused on the eye E, but optical axes of the eye E and the axes-aligning-focusing optical system 15 are not aligned with each other, the images of the eye E and the spots of the optical axes-aligning beams are clearly displayed on the monitor, however, not disposed in the center of the image displayed on the monitor as shown in FIG. 13(a). Therefore, the signal, corresponding to the spot images, detected by the light receiving sensor 13 on X-axis thereof does not have such a high peak as exceeding the reference value TL set in the comparator 31 as shown in FIG. 13(b) and the high level and low level signals produced in the comparator 31 have no pulse signals as shown in FIG. 8(c).

When the optical axes of the eye E and the optical axes-aligning-focusing system 15 are aligned with each other, but the beams emitted by the axes-aligning-focusing optical system are not focused on the eye E, the image of the eye E is displayed in the center of the monitor screen, but blurred. In particular, the spot images $P_5$ corresponding to the spot images $P_1$, $P_2$ and $P_6$ corresponding to the spot images $P_3$, $P_4$ are not clearly displayed on the monitor screen. In more detail, the spot images $P_1$, $P_2$ and $P_3$, $P_4$ of the four optical axes-aligning beams look as though $P_1$ and $P_2$, and $P_3$ and $P_4$ are connected to each other. Accordingly, as shown in FIG. 14(b), the peaks $PL_5$ and $PL_6$ of the signals detected by the light receiving sensor 13 on the X-axis thereof do not have clear two peaks which are separated. Each of the signals which exceed the reference value have only one pulse $PS_5$ $PS_6$, respectively as shown in FIG. 14(c). That is, one signal is obtained from the comparator 31 in the region between the scanning start point in X-axis on the left side thereof and Y-axis, and one signal is obtained from the comparator 31 in the region between Y-axis and the scanning termination point in X-axis on the right side thereof. Accordingly, in this case, the level of the signal outputted from the left side-spot detecting circuit 37 is low when a signal outputted from the Y-axis generating circuit 35 is inputted to the AND circuit 41. Thus, the signal is not outputted from the AND circuit 41. That is, it is decided in this case that an in-focus state cannot be detected.

When optical axes-aligned and in-focus states are obtained, the counter 39 calculates the distance between the spot image $P_1$ and Y-axis, and the counter 38 calculates the distance between the spot image $P_4$ and Y-axis.

As described above, according to the second embodiment as well, watching the image displayed on the monitor screen, an operator adjusts the distance between the eye E and the apparatus by moving the main body of the apparatus lengthwise and widthwise so as to alter the condition shown in FIG. 13 or FIG. 14 to the condition shown in FIG. 12. When the state shown in FIG. 12 is obtained, i.e., when optical axes-aligned and in-focus states are detected, the measuring of the refractive power of the eye E is automatically started. Thus, the automatic refractometer is capable of measuring the refractive power of the eye E in an appropriate measuring timing.

What is claimed is:

1. An optical measuring apparatus for examining an eye having:
   (1) a measuring light projecting system for projecting a measuring light on an eye;
   (2) a measuring light receiving system including a light receiving sensor which receives a light reflected by the eye;
   (3) optical axes-aligning-focusing means including an optical axes-aligning-focusing system for aligning the optical axes of said apparatus and the eye with each other and focusing the light emitted by said apparatus on the eye; and
   (4) measuring means for projecting a measuring light on the eye and measuring the eye based on a light reflected by the eye and received by said measuring optical system;
   said optical measuring apparatus being characterized in that:
   (1) said light receiving sensor is so disposed that the optical axis of said measuring light receiving system passes through the intersection of a X-axis and a Y-axis provided on said light receiving sensor;
   (2) said axes-aligning-focusing optical system has:

(a) a pair of optical axes-aligning light source means for projecting beams on the eye, and (b) said pair of optical axes-aligning light source means for projecting fine beams on the cornea of the eye is disposed so that said light source means are asymmetrical with respect to said optical axis of said light receiving optical system in a direction of said X-axis and that the beam reflected by the cornea of the eye is received by said light receiving sensor only when an in-focus state is substantially obtained and an axes-aligning error is extremely small; and (3) said optical axes-aligning-focusing means includes:

(a) first comparing means for comparing the level of signals representing images of two beams reflected by the cornea and received by said light receiving sensor with a reference value, (b) first discriminating means for discriminating whether or not said images are received by said light receiving sensor on the X-axis thereof when the level of said signals is discriminating to exceed the reference value, (c) calculating means for calculating the distance between the two images of the beams reflected by the cornea received by said light receiving sensor and the Y-axis of said light receiving sensor, and (d) second comparing means for comparing two distances calculated by said calculating means with each other and outputting a signal indicating the start of the projection of the measuring light if the difference between the two calculated distances is in the tolerance.

2. An optical measuring apparatus for examining an eye having:

(1) a measuring light projecting system for projecting a measuring light on an eye;

(2) a measuring light receiving system including a light receiving sensor which receives a light reflected by the eye;

(3) optical axes-aligning-focusing means including an optical axes-aligning-focusing system for aligning the optical axes of said apparatus and the eye with each other and focusing the light emitted by said apparatus on the eye; and (4) measuring means for projecting a measuring light on the eye and measuring the eye based on a light reflected by the eye and received by said measuring optical system;

said optical measuring apparatus being characterized in that:

(1) said light receiving sensor is so disposed that the optical axis of said measuring light receiving system passes through the intersection of a X-axis and a Y-axis provided on said light receiving sensor;

(2) said optical system has:

(a) a pair of optical axes-aligning light source means for projecting beams on the eye, and (b) said pair of optical axes aligning light source means for projecting fine beams on the cornea of the eye is disposed so that said light source means are symmetrical with respect to said optical axis of said light receiving optical system in a direction of said X-axis and that the beam reflected by the cornea of the eye is received by said light receiving sensor only when an in-focus state is substantially obtained and an axes-aligning error is extremely small; and (3) said optical axes-aligning-focusing means includes:

(a) a comparator which compares the level of an image signal outputted from said light receiving sensor with a reference value so as to output, as a pulse signal, an image signal indicating the image of first and second cornea-reflected beams corresponding to beams emitted by first and second optical axes-aligning light source means, (b) a synchronizing signal separator circuit for separating a synchronizing signal outputted together with the image signal from said light receiving sensor into a horizontal synchronizing signal and a vertical synchronizing signal, (c) a circuit for generating an X-axis reference signal indicating that the image signal outputted from said light receiving sensor corresponds to an image disposed on the X-axis of said light receiving sensor based on the horizontal synchronizing signal and the vertical synchronizing signal outputted from said synchronizing signal separator circuit, (d) a first AND circuit which outputs a pulse signal in response to the pulse signal outputted from said comparator and the X axis reference signal, (e) a first reflected image detecting circuit which outputs a pulse signal when a first pulse signal is counted while counting the pulse signal outputted from said first AND circuit, (f) a circuit for generating a Y-axis reference signal indicating that the image signal outputted from said light receiving sensor corresponds to an image on the Y-axis of said light receiving sensor based on the horizontal synchronizing signal outputted from said synchronizing signal separator circuit, (g) a second AND circuit which outputs a stop signal in response to the pulse signal outputted from said first reflected image detecting circuit and the Y-axis reference signal outputted from said circuit for generating the Y-axis reference signal, (h) a first circuit for detecting the distance between a reflected image and the Y-axis which starts a counting in response to the pulse signal outputted from said first AND circuit and steps the counting in response to the stop signal outputted from said second AND circuit so as to output a first distance signal indicating the distance between a first cornea-reflected image and the Y-axis, (i) a second reflected image detecting circuit which outputs a pulse signal when a second pulse signal is counted while counting the pulse signal outputted from said first AND circuit, (j) a second counter for detecting the distance between a reflected image and the Y-axis which starts a counting in response to the Y-axis reference signal outputted from said Y-axis reference generating circuit and stops the counting in response to the pulse signal outputted from said second reflected image detecting circuit so as to output a second distance signal indicating the distance between a second cornea-reflected image and the Y-axis, and (k) a comparing circuit which compares a first distance and a second distance with each other based on the first and second distance signals outputted from said first and second circuits for detecting the distance between a reflected image and the Y-axis and outputs to said apparatus a signal indicative of the start of the projection of a measuring light if the difference between the values of the first distance and the second distance is less than a tolerance.

3. An optical measuring apparatus for examining an eye having:
(1) a measuring light projecting system for projecting a measuring light on an eye;
(2) a measuring light receiving system including a light receiving sensor which receives a light reflected by the eye;
(3) optical axesaligning-focusing means including an optical axes-aligning focusing system for aligning the optical axes of said apparatus and the eye with each other and focusing the light emitted by said apparatus on the eye; and
(4) measuring means for projecting a measuring light on the eye and measuring the eye based on a light reflected by the eye and received by said measuring optical system;
said optical measuring apparatus being characterized in that:
(1) said light receiving sensor is so disposed that the optical axis of said measuring light receiving system passes through the intersection of X-axis and Y-axis provided on said light receiving sensor;
(2) said optical axes-aligning-focusing system
  (a) has a pair of optical axes-aligning light source means for projecting a pair of beams close to each other and arranged in a direction of said X-axis toward the eye, and
  (b) said pair of optical axes-aligning light source means is disposed to be symmetrical with respect to said optical axis in a direction of said X-axis; and
(3) said optical axes-aligning-focusing means includes
  (a) first discriminating means for discriminating whether or not cornea-reflected images are formed on said light receiving sensor on the X-axis thereof,
  (b) second discriminating means for discriminating whether or not the cornea-reflected images, formed on said light receiving sensor on the X-axis thereof and detected by said first discriminating means, do not overlap with each other and are separate from each other,
  (c) calculating means for calculating the distance between the Y-axis of said light receiving sensor and each of the two images disposed on both outer sides among the cornea-reflected images received by said light receiving sensor on the X-axis thereof, and '(d) comparing means for comparing two distance calculated by said calculating means with each other and outputting a signal indicating the start of the projection of the measuring light if the difference between the two calculated distances is less than the tolerance.

4. An optical measuring apparatus for examining an eye having:
(1) a measuring light projecting system for projecting a measuring light on an eye;
(2) a measuring light receiving system including a light receiving sensor which receives a light reflected by the eye;
(3) optical axes-aligning-focusing means including an optical axes-aligning-focusing system for aligning the optical axes of said apparatus and the eye with each other and focusing the light emitted by said apparatus on the eye; and
(4) measuring means for projecting a measuring light on the eye and measuring the eye based on a light reflected by the eye and received by said measuring optical system;
said optical apparatus being characterized in that:
(1) said light receiving sensor is so disposed that the optical axis of said measuring light receiving system passes through the intersection of X-axis and Y-axis provided on said light receiving sensor;
(2) said optical axes-aligning-focusing system
  (a) has a pair of optical axes-aligning light source means for projecting a pair of beams close to each other and arranged in a direction of said X-axis toward the eye, and
  (b) said pair of optical axes-aligning light source means is disposed to be symmetrical with respect to said optical axis in a direction of said X-axis; and
(3) said optical axes-aligning-focusing means includes:
  (a) a comparator which compares the level of an image signal outputted from said light receiving sensor with a reference value so as to output, as a pulse signal, an image signal indicating the image of first and second cornea-reflected beams corresponding to first and second beams emitted by first and second optical axes-aligning light source means and third and fourth cornea-reflected lights corresponding to third and fourth beams emitted by a second optical axes-aligning light source means,
  (b) a synchronizing signal separator circuit for separating a synchronizing signal outputted together with the image signal from said light receiving sensor into a horizontal synchronizing signal and a vertical synchronizing signal,
  (c) a circuit for generating an X-axis reference signal indicating that the image signal outputted from said light receiving sensor corresponds to an image on the X-axis of said light receiving sensor based on the horizontal synchronizing signal and the vertical synchronizing signal outputted from said synchronizing signal separator circuit,
  (d) a first AND circuit which outputs a pulse signal in response to the pulse signal outputted from said comparator and the X-axis reference signal,
  (e) a first reflected image detecting circuit which outputs a pulse signal when a second pulse signal is counted while counting the pulse signal outputted from said first AND circuit,
  (f) a circuit for generating a Y-axis reference signal indicating that the image signal outputted from said light receiving sensor corresponds to an image on the Y-axis of said light receiving sensor based on the horizontal synchronizing signal outputted from said synchronizing signal separator circuit,
  (g) a second AND circuit which outputs a stop signal in response to the pulse signal outputted from said first reflected image detecting circuit and the Y-axis reference signal outputted from said circuit for generating a Y-axis reference signal, (h) a first circuit for detecting the distance between a reflected image and Y-axis which starts a counting in response to the pulse signal outputted from said first AND circuit and stops the counting in response to the stop signal outputted from said second AND circuit so as to output a first distance signal indicating the distance between a first cornea-reflected image and Y-axis, (i) a second reflected image detecting circuit which outputs a pulse signal when a fourth pulse signal is counted while counting the pulse signal outputted from said first AND circuit, (j) a second counter for detecting the distance between a reflected image and the Y-axis which starts a counting in response to the Y-axis reference signal outputted from said Y-axis reference generating circuit and stops the counting in response to the pulse signal outputted from said second reflected image detecting circuit so as to output a second distance signal indicating the distance between a second cornea-reflected image and the Y-axis, and (k) a comparing circuit which compares a first distance and a second distance with each other based on the first and second distance signals outputted from said first and second circuits for detecting the distance between a reflected image and Y-axis and outputs to said apparatus a signal indicative of the start of the projection of a measuring light if the difference between the values of the first distance and the second distance is less than a tolerance.

* * * * *